United States Patent
Rodriguez-Ponce et al.

(10) Patent No.: US 11,678,836 B2
(45) Date of Patent: Jun. 20, 2023

(54) METHOD AND APPARATUS FOR ESTIMATING TEMPERATURE IN A BODY

(71) Applicant: Brainlab AG, Munich (DE)

(72) Inventors: Maria Inmaculada Rodriguez-Ponce, Feldkirchen (DE); Stephan Mittermeyer, Munich (DE)

(73) Assignee: Brainlab AG, Munich (DE)

( * ) Notice: Subject to any disclaimer, the term of this patent is extended or adjusted under 35 U.S.C. 154(b) by 1120 days.

(21) Appl. No.: 16/273,316

(22) Filed: Feb. 12, 2019

(65) Prior Publication Data

US 2019/0167180 A1   Jun. 6, 2019

Related U.S. Application Data

(62) Division of application No. 13/575,637, filed as application No. PCT/EP2010/050977 on Jan. 28, 2010, now abandoned.

(51) Int. Cl.
| | |
|---|---|
| *A61B 5/00* | (2006.01) |
| *A61B 5/01* | (2006.01) |
| *A61B 5/055* | (2006.01) |
| *G09B 23/28* | (2006.01) |
| *G16H 20/40* | (2018.01) |
| *A61N 1/40* | (2006.01) |
| *G01R 33/48* | (2006.01) |
| *G01R 33/563* | (2006.01) |

(52) U.S. Cl.
CPC .............. *A61B 5/417* (2013.01); *A61B 5/015* (2013.01); *A61B 5/055* (2013.01); *G09B 23/28* (2013.01); *G16H 20/40* (2018.01); *A61N 1/403* (2013.01); *G01R 33/4804* (2013.01); *G01R 33/56366* (2013.01)

(58) Field of Classification Search
None
See application file for complete search history.

(56) References Cited

U.S. PATENT DOCUMENTS

| | | |
|---|---|---|
| 5,224,492 A | 7/1993 | Takahashi et al. |
| 6,312,391 B1 | 11/2001 | Ramadhyani et al. |
| 2010/0250209 A1 | 9/2010 | Pearson et al. |

OTHER PUBLICATIONS

Farace et al. (Phys. Med. Biol. 42 (1997) 2159-2174) (Year: 1997).*
Krol et al. (IEEE Int. Symp. on Biomedical Imaging: from Nano to Macro, Apr. 2006, pp. 852-855). (Year: 2006).*
International Search Report and Written Opinion for International Application No. PCT/EP2010/050977 dated Nov. 22, 2010 (21 pages).
Craciunescu et al. "Discretizing Large Traceable Vessels and Using DE-MRI Perfusion Maps Yields Numerical Temperature Contours that Match the MR Noninvasive Measurements," Medical Physics, AIP, vol. 28, No. 11, Nov. 2011 (pp. 2289-2296).
Zhu et al., "Theoretical Stimulation of Temperature Distribution in the Brain During Mild Hypothermia Treatment for Brain Injury, Medical and Biological Engineering and Computing", vol. 39, No. 6, Nov. 2001 (pp. 681-687).
Ma et al., "A Monte Carlo Dose Calculation Tool for Radiotherapy Treatment Planning", Phys. Med. Biol. 47 (2002), pp. 1671-1689.
Liu, et al., "Pilot Point Temperature Regulation for Thermal Lesion Control During Ultrasound Thermal Therapy", Medical and Biological Engineering and Computing, 2004, vol. 2, pp. 178-188.

\* cited by examiner

*Primary Examiner* — Pablo S Whaley
(74) *Attorney, Agent, or Firm* — Tucker Ellis LLP

(57) ABSTRACT

The invention relates a method and an apparatus of predicting or planning a temperature distribution (52) in a body. The method comprises the steps of: a) obtaining a model of the body (50) related to a temperature transport mechanism or temperature distribution (52) in the body; b) simulating an application of heat to at least a part of the body such as targeted tissue; c) determining and/or predicting the temperature (52) or heat distribution in at least a part of the body using the model of the body (50).

20 Claims, 4 Drawing Sheets

METHOD AND APPARATUS FOR ESTIMATING TEMPERATURE IN A BODY

CROSS-REFERENCE TO RELATED APPLICATIONS

This application is a divisional of application Ser. No. 13/575,637, filed on Oct. 22, 2012, which is a National Stage Entry of International Application No. PCT/EP2010/050977 filed on Jan. 28, 2010 and published in the English language.

FIELD

The present invention relates to a method and to an apparatus for estimating a temperature distribution in a body such as a biologic tissue or lifeless material.

BACKGROUND

The problem of temperature measurement in a body, such as biologic or living tissue, generally goes with an invasive process. However, the introduction of a foreign body into the tissue leads to obvious inconveniences. Until now, several physical processes have been considered with the aim of solving this problem.

Microwave radiometry for example appears to be well suited for temperature investigations of moderately deep-seated tissues. However, a major drawback of this process is related to the noise power emitted by a lossy material, which limits the depth of tissues under investigation.

In active ultrasound methods, a search for appropriate parameters for temperature sensing is a very difficult task. Ultrasound speed in tissue varies with temperature because the density of the tissue varies with temperature. However, the density varies also due to temperature independent tissue properties such as fat or water content, multipath-scattering and multiple reflections.

SUMMARY

It is an object of the invention to provide a reliable method and apparatus for predicting or calculating the temperature in a body, such as for example biologic tissue.

This object is solved by the method and the apparatus as defined in the independent claims. Preferred embodiments are defined in the dependent claims.

According to an aspect of the invention, a method of predicting or planning a temperature distribution in a biologic tissue such as a body is suggested. The temperature distribution is related to the space and time dependency of the temperature. The space dependency may concern the variation of temperature inside the body as a function of position. The time dependency may concern the variation of temperature as a function of time. The temperature may refer to an absolute value of the temperature, as well as to a relative value indicating a temperature value at a first position and/or first time as being higher or lower than or equal to a temperature value at a second position and/or second time.

Predicting a temperature distribution may refer to determining, calculating or obtaining the value distribution at present time, as well as forecasting the distribution at a future time. Planning a temperature distribution may refer to setting or changing parameters determining the process of heat flow in the body, such as the power of a physically available or simulated heat source, to obtain a desired temperature distribution in the body. Planning a temperature distribution may also refer to simulating a heat transfer into the body to arrange or prepare parameters determining the process of heat flow in the body for a subsequent process such as a surgical process.

The method comprises the steps of obtaining a model of the body, simulating an application of heat to at least a part of the body and determining the temperature distribution in at least a part of the body.

The model of the body obtained in the initial step is related to or directed to or describing a temperature transport mechanism or temperature distribution in the body. The model may basically comprise a 2D and/or 3D signal distribution in the body related to a physical feature of the body, such as perfusion or blood flow or agent concentration or diffusion coefficients. A signal value at a point in space and a time complies with a corresponding value of the physical feature of the body at the specified point and time.

Simulating an application of heat may refer to simulating at the boundary of a simulation space including at least a part of the body a boundary condition for the heat distribution such as a heat source or a heat distribution at the boundary of the simulation space. Simulating an application of heat may additionally refer to simulating the heat propagation inside the simulation space. The simulation space may comprise for example the whole body or the body plus a part of the body environment or only a part of the body including a targeted tissue or a part of the body without the targeted tissue or only the targeted tissue. The targeted tissue may be a tumour or a simulated tumour or a tissue affected by another disease.

Simulating an application of heat may comprise simulating heat from a simulated heat source such as an electromagnetic field or any other heat transport carrier to the body. The simulated heat application may be for example focal ultrasound, laser beam, catheter, x-ray, infrared, microwaves, gamma radiation, or any other radiation with a wave length suitable to apply thermal energy to tissue, nano particles, colloids, or liposome.

In so doing, applying heat to the body can refer to an application of heat which is not physically performed, but simulated.

Determining the temperature distribution in the body may refer to determining and/or predicting the temperature or heat distribution in at least a part of the body using the model of the body, preferably by taking into account the physical or simulated heat source. Advantageously, the information on the physical or expected temperature distribution can facilitate a treatment planning where thermal variations in tissue are expected, for example in radiotherapy, to redefine and/or control the heat monitoring set-up.

In an embodiment, determining and/or predicting the temperature or heat distribution in at least a part of the body may comprise performing thermodynamic simulations to simulate the heat propagation and/or distribution in the body. For this purpose a thermodynamic framework such as a computer aided design system for thermodynamic simulations can be provided being able to simulate the heat propagation and/or distribution in the body. The thermodynamic framework is a computer program able to perform heat flow simulations in a simulated, preferably discretized, body or tissue worked up to be processed in the thermodynamic framework.

For enabling the simulation of an application and/or propagation of heat to at least a part of the body, the body model is supposed to be entered into the thermodynamic framework. Entering the model including a geometrical structure of the body as well as other input data such as boundary conditions and tissue parameters into the framework may enable the program or framework to simulate a heat flow in the body similar to a real heat flow.

In an optional embodiment, a series of one or more images or imaging sequences of the body under the application of heat such as an electromagnetic field or any other heat transport carrier can be obtained. The images can also be obtained without the application of heat, thus describing an initial state of the body before applying heat to the body.

The images of a series may be obtained at subsequent, preferably equidistant, time steps, thus perceiving or generating a time dependency of the tissue parameters or heat distribution in the body. When dealing with 2D images, the series of images shows the time dependency of 2D tissue parameters or heat distribution in a plane cutting the body.

An imaging sequence of the body may refer to several 2D images in parallel, preferably equidistant, planes cutting the body basically simultaneously to obtain a 3D image of the body. Consequently, the images of a series of imaging sequences may refer to a time dependency of the 3D tissue parameters or heat distribution in the body.

Determining the temperature or heat distribution in at least a part of the body may also comprise adding the series of images or imaging sequences to the model of the body. Adding an image to the model may refer to obtaining from a signal distribution of an image, representing a physical feature of the body such as a concentration of contrast agent in blood, a signal distribution representing another physical feature of the body such perfusion. Thus, the model of the body may comprise a data set representing 2D and/or 3D time dependent data, for example perfusion distributions, of the body. Feeding the model into the thermodynamic framework of the body enables the calculation of the heat and/or temperature distribution in the body. The model can be amended at any time by adding supplementary data to the model, thus enabling to take into consideration new information such as a thermoablation or a surgical intervention on the targeted tissue According to an aspect of the invention, a method of controlling or monitoring a temperature distribution in a body is suggested. The body can be the whole physical body of a patient or animal, or a part of the body such as an organ, for example liver, knee or brain, a or a lump of biological, human or animal, preferably living, tissue.

Controlling the temperature distribution in the body may be valuable with a process of heat treatment of the body, especially thermal ablation therapy. Such a therapy may be applied to effect local overheating of a preferably deep-seated human tumour for destructing the tumour, to cure a cardiac arrhythmia such as supraventricular tachycardia or Wolff-Parkinson-White, to treat a coronary heart disease, to eliminate marrow cells in preparation for a bone marrow transplant, or to treat neurological disorders, for example Parkinson's disease.

Controlling the temperature distribution in the body may consequently refer to setting up the parameters of a heat source applying heat to the body so that a defined or desired spatial distribution or temporal progression of heat in the body is obtained. With tumour ablation or nekrosis for example the desired temperature distribution can be as far as possible at least 80 degrees Celsius inside the tumour and less than 41 degrees outside the tumour.

Monitoring the temperature distribution may refer to watching and/or surveying and/or forecasting the temperature distribution in the body with the scope of estimating whether the current and/or forecasted temperature distribution in the body corresponds to the defined or desired temperature distribution.

The method comprises the steps of obtaining a model of the body, applying heat to the body and determining the temperature distribution in the body.

Obtaining a model of the body may concern a model related to or directed to or describing a temperature transport mechanism or temperature distribution in the body. The model may basically comprise a 2D and/or 3D signal distribution in the body related to a physical feature of the body, such as perfusion or blood flow or agent concentration or diffusion coefficients. A signal value at a point in space and a time complies with a corresponding value of the physical feature of the body at the specified point and time. The temperature or heat distribution in the body may correlate with the distribution of the physical feature of the body, so that a signal distribution in the body may correlate with the temperature or heat distribution in the body. The model comprises data which is not influenced by any application of heat.

Applying heat to the body may refer to bringing a heat source to or in the vicinity of the body so that the heat may reach or penetrate the body. The heat source can be the source of an electromagnetic field or any other heat transport carrier. Such a heat transport carrier may be for example focal ultrasound, laser beam, catheter, x-ray, infrared, microwaves, gamma radiation, or any other radiation with a wave length suitable to apply thermal energy to tissue, nano particles, colloids, or liposome.

The application of heat to the body may concern the whole body or the body plus a part of the body environment or only a part of the body including a targeted tissue or a part of the body without the targeted tissue or only the targeted tissue. The targeted tissue may be a tumour or a simulated tumour or a tissue affected by any other disease.

From the parameters of the heat source, a thermal boundary condition related to the body can be obtained, for example the heat and/or temperature distribution at the boundary of a tissue under consideration, for example the outer skin of the body or part of the body such as an organ. If optionally the heat source transmits heat so, that the heat is supposed to focus in the targeted tissue, for example in the volume of a tumour, then the heat distribution on the tissue under consideration permits an appropriate calculation of the heat distribution using the thermodynamic simulation framework. Reference is made to L. Zhu and C. Diao.—Pilot point temperature regulation for thermal lesion control during ultrasound thermal therapy. Med. Biol. Eng.—.Compt., 2001, 39, 681-687 [10] which is included by reference for details of calculating the heat distribution inside brain tissue accounting for an arbitrary heat source. Relevant physical parameters like specific heat capacity of each point in space can be determined by MRI (e.g. presence of water as prominent factor to modify the specific heat capacity). For example, in paper [11] the authors describe the calculation of the electrical conductivity in brain tissue with MRI techniques. It exists a direct relation between electrical and thermal conductivity which is well known (see Wiedmann-Franz Law). Further parameters may be determined by the use of a reference body. As parameters may vary in different types of tissue, those types of tissue may be segmented and clustered in the MR images to relate those clusters to values determined by using reference bodies. To account for heat transfer, blood volume and blood flow derived from perfusion imaging can be incorporated. The directional heat transport through a voxel can be determined by the (averaged) thermal conductivity value, the dimensions of the voxel and $\Delta T$. [10]

L. Zhu and C. Diao.—Pilot point temperature regulation for thermal lesion control during ultrasound thermal therapy. Med. Biol. Eng. Compt., 2001, 39, 681-687[11] David S. Tuch, Van J. Wedeen, Anders M. Dale, John S. George, and John W. Belliveau—Conductivity tensor mapping of the human brain using diffusion tensor MRI. PNAS u Sep. 25, 2001 u vol. 98 u no. 20 u 11697-11701

Determining the temperature distribution in the body may refer to determining and/or predicting the temperature or heat distribution in the body using the model of the body and the thermal boundary condition which takes into account the heat source. Advantageously, the information on the current or forecasted temperature distribution can facilitate a treatment planning where thermal variations in tissue are expected, for example in radiotherapy, to redefine and/or control the heat monitoring set-up.

In a preferable embodiment, a dose of contrast agent or tracer such as gadolinium, flavones acetic or 5,6-dimethyl-xantenone-4-acetic acid or any perfluorocarbon or derivative thereof can be fed into the body. The contrast agent can be administered for example orally or as a bolus intravenous injection. Feeding the contrast agent is particularly advantageous with a magnetic resonance technique focused on imaging the blood perfusion in the body.

The characterization of tumor vasculature with magnetic resonance (MR) contrast agents can use a low-molecular-weight paramagnetic gadolinium (III) chelate that extravasates in the absence of a blood-brain barrier, but cannot permeate viable cell membranes. Such a contrast agent alters the MR signal due to his effect on the relaxation processes of tissue water protons. The unpaired elections in this contrast agent provide an efficient mechanism for spin-lattice relaxation of water protons when the water molecule binds in the first or second coordination sphere of the contrast agent complex. As a consequence, the spin-lattice relaxation rate $R_1$, which is the reciprocal of the first-order time constant for spin-lattice relaxation $T_1$, is decreased in proportion to the contrast agent concentration. The decreased $R_1$ leads to an increase in MRI signal intensity.

In an optional embodiment, one or more temperature probes can be attached to a specific part of the body to measure or obtain the absolute temperature of that part of the body. Such a probe can be placed onto the body, for example on the skin of a patient. The probe can also be placed into or inside of the body, for example by means of a catheter. The measured temperature can be regarded as a reference temperature and can be used to calibrate a temperature distribution obtained from the model of the body.

In an embodiment, obtaining a model of the body can comprise obtaining a series of one or more images or imaging sequences of the body preferably enabling the calculation of perfucion and/or diffusion properties of the body. The series showing images obtained at subsequent time steps can enable the model to show dynamic processes such as a spin-lattice relaxation of water protons, which is typical to magnetic resonance imaging (MRI). At the dynamic contrast enhanced (DCE) MRI, for example, the signal distribution of the images may lead to a perfusion distribution of the body.

In an embodiment, a perfusion model of the body obtained with MRI, preferably with DCE-MRI, can be used as the model of the body. DCE-MRI involves acquisition of a series of $T_1$-weighted images before, during, and after feeding of the contrast agent. The change in signal over time measured by DCE-MRI reflects the exchange of contrast agent between vascular space and, since the contrast agent does not penetrate viable cells, extravascular-extracellular space. A blood perfusion value at a point in space and time inside the body can be obtained from a pixel value of an image at that point in space and time, the pixel value representing preferably a blood plasma contrast agent concentration at that point in space and time.

The exchange depends upon the capillary blood flow or perfusion (F), initial extraction ratio (E), which is an index characterizing the tissue, Hematocrit ($H_{ct}$), contrast agent distribution volume, which is commonly assumed to equal the fractional volume ($V_e$) of extravascular-extracellular space (EES), contrast agent concentration in tissue ($C_t$) as a function of time (t), contrast agent concentration in blood plasma ($C_p$), and transfer constant $K^{trans}$. The contrast agent concentration in tissue can thus be written as:

$$\frac{dC_t}{dt} = EF(1 - H_{ct})\left(C_p - \frac{C_t}{V_e}\right)$$

or $$C_t(t) = F(1 - H_{ct})\int C_p(\tau)e^{-k_{ep}(t-\tau)}d\tau$$

whereas $K^{trans}=F(1-H_{ct})$. Equation (1) is part of a mixed flow permeability-limited model and equation (2) is part of a generalized kinetic model (Toffs. et al. [1]). Other formulations of the contrast agent concentration, depending on the known tissue parameters and the boundary conditions, are according to [1] also possible. [1] Paul S. Toils, Gunnar Brix, David L. Buckley, Jeffrey L. Evelhoch, Elizabeth Henderson, Michael V. Knopp, Henrik B. W. Larsson, Ting-Yim Lee, Nina A. Mayr, Geoffrey J. M. Parker, Ruediger E. Port, June Taylor, and Robert M. Weisskoff—Estimating Kinetic Parameters From Dynamic Contrast-Enhanced T1-Weighted MRI of a Diffusable Tracer: Standardized Quantities and Symbols, JOURNAL OF MAGNETIC RESONANCE IMAGING 10:223-232 (1999)

Alternatively, a perfusion model of the body obtained with delayed contrast enhanced MRI or with magnetic resonance spectroscopy, can be used as the model of the body.

In another embodiment, a perfusion model of the body obtained with computer or x ray tomography can be used as the model of the body. Analogously to classical x ray imaging, the computer tomography is based on the weakening of x rays while passing through the examined tissue. The measurements of radiation attenuation caused by the tissue are recorded in a large number of projections. In addition to the purely anatomical information, reference on the blood perfusion can be also obtained. To this end a time sequence of images of the considered anatomical region is obtained. If during such a dynamic investigation a contrast agent is fed to the body, it is possible to obtain the time and space dependent distribution of the perfusion in the tissue (habilitation treatise [2])

[2] Hans-Jorg Wittsack—Ermittlung von Perfusionsparametern anhand dynamischer, kontrastmittelgestutzter Schnittbildverfahren, Habilitationsschrift, Dusseldorf 2007

In an embodiment, a model based on diffusion coefficients obtained with magnetic resonance imaging can be used as the model of the body. For this purpose the temperature dependence of the translational self-diffusion coefficient and viscosity are established on the basis of the Stokes-Einstein relationship (Simpson, Carr [1]). When an object is subjected to changing temperatures, these temperature changes induce changes in the diffusion coefficient which can be calculated from differentiating the Stokes-Einstein equation as long as the variations of the activation energy with the temperature are small.

The effect of molecular diffusion in the presence of a magnetic field gradient on MR spin-echo signals is well known. Diffusion produces a pure amplitude attenuation of the MR signal due to the loss of phase coherence between processing spins produced by their random walk through the gradient. This amplitude attenuation depends only on the diffusion coefficient D and the gradient. Thus it is possible to obtain the self-diffusion coefficient with MR1 measurements, from which the temperature distribution can be obtained.

In an embodiment, a model based on proton-frequency-shift alterations obtained with magnetic resonance imaging can be used as the model of the body. With the PRF-shift method of thermometry, the phase-shift sensitivity or a thermal coefficient is generally modeled as being a function of the gyromagnetic ratio for H nuclei, the magnetic field strength and the apparent PRF-thermal coefficient containing contributions from changes in the electron screening constain and magnetic susceptibility. In a conductive material, a transmitted magnetic field will undergo amplitude attenuation and phase retardation, giving rise to a variation in tip angles and phase over the body. In particular, the spatial nature of the phase variation in the MR image will depend on the material properties and the imaging coil(s) used to transmit and receive the RF signal. Temperature induced changes in the material's electrical conductivity and, to a lesser extent, permittivity will result in changes in the wave number of the RF wave and, thus, the phase-retardation of the magnetic field (see [4], [5], [6], [7]).

[4] Y. Ishihara, et al. SMRM Proc. 4803 (1992)[5] J. C. Hindman J Chem. Phys. 44(12):4582-4592 (1966)[6] J. Depoorter MRM 34:359-367 (1995)[7] P. Bottomley, et al. Phys. Med. BioZ. 23(4):630-643 (1978)

In another embodiment, a reference model directed to a transport mechanism or reference temperature distribution in a reference body can be obtained from a data base. The reference body has well known tissue parameters and distributions of physical features such as perfusion or temperature. The data of the reference body can be used to calibrate the values of a relative temperature distribution obtained from the model of the body.

In an embodiment, a set of tissue parameters can be obtained from the images of the body under consideration. The tissue parameters can be for example the permeability surface area product of the endothelium and/or fractional size of the extravascular extracellular space and/or hematocrit and/or total permeability of capillary wall and/or permeability surface area product per unit mass of tissue and/or any other tissue parameter used in the work of Tofts et. al. [1]. Any other tissue parameters related directly or indirectly to the distribution of contrast agent or to another physical entity correlated with the signal distribution shown in the images of the body can be obtained from the model of the body. The method of obtaining the tissue parameter may consist in establishing a system of preferably linear equations from the equations (1) or (2) or from similar equations determining a relationship between the measured signals of the images and the physical feature correlated with the signals. The procedure may consist in a) applying for example equation (1) to several contrast agent concentrations correlated with corresponding signal pixels of a image, b) combining the obtained equations to a system of over-determined linear equation having the tissue parameters as unknowns, and e) solving for the unknowns by an optimization method such as a least squares method.

In another embodiment, an individualized model directed to a temperature transport mechanism or temperature distribution mechanism in the body under consideration can be obtained from the reference model and the tissue parameters. If for example the geometry of the reference body is similar to that of the body under consideration, then a 3D rigid and/or non-rigid registration of the reference model to the model under consideration can be performed. Subsequently, the distribution of the physical feature, for example perfusion, of the reference model, can be adapted to the model under consideration by taking into consideration the differences between the tissue parameters of the body under consideration and the reference body.

With a perfusion model as the model of the body, a perfusion distribution of the body composing the perfusion model can initially be obtained from a signal distribution of the images by applying the framework of Tofts et. al. [1] expressed for example by the equations (1) or (2).

Subsequently, the temperature at a point in space and time can be determined from the perfusion at that point in space and time. To achieve this, a tabular dependency of temperature in space and time from the blood perfusion at that point in space and time can be used. As well, a tabular dependency of a temperature gradient or a time dependent change of the temperature at a point from the blood perfusion at that point can be used. Since the reference body has well known tissue parameters and distributions of physical features such as perfusion or temperature, the value pairs perfusion/temperature, or perfusion/temperature gradient, or perfusion/time dependent change of the temperature, can be obtained from the reference body. The reference tables obtained this way can be stored in the data base.

If a temperature value is required which is not comprised in the reference table, numerical interpolation with piecewise linear or nonlinear functions, e.g. cubic splines, or extrapolation, can be used.

Preferably, obtaining the temperature at a point in space and time from the perfusion at that point in space and time can be performed using a bioheat equation such as the Pennes equation. This relation is based on the fact, that heat transfer at any given point in the tissue is directly proportional to the local temperature gradient. Taking into consideration the time dependency of the heat transfer, the energy balance for a considered body can be written as:

$$\frac{\partial T}{\partial t} = \frac{1}{\rho c_v} \left[ k_T \nabla^2 T - C(T_b) \right]$$

The equation (3) is known as bioheat equation. Where K is the thermal conductivity, rho is the blood density, Cv is the specific heat of blood and C the local blood perfusion rate (called F in equation (1)). See paper [10] for a detailed description of the utility of this equation that explains the temperature distribution in brain tissue. Additional terms in the right-hand side can appear depending on different heat sources (like external radiation field, etc). The dependency of the temperature from a signal distribution obtained from images or from the model of the body can be determined according to the following sequence: a) obtaining a perfusion distribution as well as the tissue parameters of the body from the signal distribution using one of the equations (1) or (2) or a similar equation, b) obtaining the temperature or heat distribution in the body from the perfusion distribution and tissue parameters using the equation (3). Note that according to Tuch et al. (reference [11]) the thermal conductivity can also be obtained by MRI techniques.

Preferably, obtaining one or more images or imaging sequences of the body can refer to applying an imaging method such as magnetic resonance, computer tomography, X-rays, or fluoroscopic imaging, to the body. The images obtained this way may refer to a state of the body before or during a therapy such as a thermal or chemo therapy, the body comprising tissue that needs to be observed such as a tumour.

Optionally, one or more images or imaging sequences of the body can be retrieved from the data base. These images may refer to a different state of the body, in which for example the body does not comprise the tumour.

In an optional embodiment, the relation between thermal and perfusion distribution inside the body is based on the thermodynamic energy balance embodied in the Pennes bioheat equation. The bioheat equation with appropriate boundary conditions yields the temperature distribution throughout the at least part of the body under consideration. Obtaining the thermal distribution can comprise, although it is not required, the steps of determining an initial perfusion distribution of the body before applying heat to the body, calculating a temperature distribution in the body based on the initial perfusion distribution and a heat power input upon commencement of the heat application, and iteratively adjusting the perfusion distribution of the body based on the calculated temperature distribution and recalculating the temperature distribution based on the adjusted perfusion distribution and the heat power.

The thermal calculation can be performed by a finite-difference method. The calculation region is divided into finite-sized sub-volumes of tissue that are taken to be sufficiently small so as to convert the differential expressions in the energy balance to algebraic expressions with an sufficient degree of approximation. An algebraic equation is thus obtained for each sub-volume of tissue. Simultaneous solution of these algebraic equations by standard linear algebra techniques yields the temperature at the center of each tissue sub-volume, which provides an approximation of the true, continuous temperature distribution in the tissue.

The time dependent variations of temperature in the body is tracked by subdividing time into short, discrete intervals or time steps, such as one second intervals in an exemplary embodiment. The numerical framework for the calculation complies with the state of the art methods common to thermodynamic simulations.

An initial condition or initial perfusion distribution of the body or targeted tissue can be determined in the first instance with DTE-MRI. This initial condition includes an initial perfusion rate distribution in the body. The initial perfusion distribution, along with a heat power input can be fed into the thermodynamic simulation framework to solve the bioheat equation to yield a temperature distribution in the body. The temperature of tissue in the body is utilized to adjust the tissue parameters of the body, since the tissue parameters are highly dependent on temperature. The relationship of the tissue parameters and temperature is based on in-vitro experimental measurements that are known in the art.

The rate of blood perfusion in the targeted tissue can be dependent on temperature, time of exposure to elevated temperatures, and the location of the targeted tissue within the body. In turn, the rate of blood perfusion affects the temperature elevation of tissue in response to continued exposure to heat. Therefore, in order to accurately model the temperature distribution in the body, the rate of blood perfusion must be continually updated for each iterative solution of the bioheat equation. Therefore, a perfusion adjustment is determined, based on the temperature and location of the targeted tissue, to adjust the perfusion rate input to the mathematical model.

In an embodiment, the calculation of the temperature distribution can used for determining a volume of necrosis in the targeted tissue based on the time and temperature relationship therein. The determination of the volume of necrosis, which can be defined as a destruction of a predetermined percentage, is also important to signify to a treating physician when therapy is complete and may be discontinued. By accurately modeling temperature and the extent of necrosis during a treatment session, the total session time can be minimized for each patient, which is highly desirable to optimize the thermal dosage received by the patient.

Calculation of the fraction of cells that have been destroyed requires knowledge of the chemical kinetic rate constant for the damage mechanism of cells in the targeted tissue, which varies strongly with temperature. The rate constant and its variation with temperature are established by comparing the predictions of the thermal model against experimentally measured temperatures in a number of patients during a thermal therapy procedure. Specifically, the rate constant can be determined using an Arrhenius rate constant model [9]. [9] Perez and Brady's principles and practice of radiation oncology, Wolters Kluwer Health, 2007

Preferably, the perfusion distribution of the body can be adjusted based on the determined volume of necrosis. The determination of a volume of necrosis may signify to a treating physician when therapy is complete and may be discontinued.

In an embodiment, the images or imaging sequences can be obtained with magnetic resonance T1-weighted gradient-echo sequences or with magnetic resonance proton-frequency-shift alterations or with x ray tomography.

In another embodiment, absolute temperature values of the body can be obtained by relating one or more reference temperature values obtained from measurements and/or from the data base to corresponding one or more temperature values of the temperature model of the body. The temperature values of the body in the data base can also rely on measurements.

In an embodiment, the calculated and/or forecasted temperature distribution within the body, especially in the targeted tissue, can be displayed and/or monitored. Displaying such information can be useful to signify to a treating physician when therapy is complete and has to be suspended or interrupted. For the display, a temperature map can be used.

The invention also relates to a computer program, which, when loaded or running on a computer, performs or supports the method or steps as set forth above. Furthermore, the invention relates to a program storage medium or a computer program product comprising such a program.

According to a further aspect, the invention relates to an apparatus or system for predicting or planning a temperature distribution in a body using a model of the body. The system comprises a imaging equipment suitable to obtain images of at least a part of the body, a data base connected to the imaging equipment suitable to store the model of the body and to retrieve the stored information and a data processing unit connected to the imaging equipment and/or to the data base. The data processing unit is capable to obtain the model directed to a temperature transport mechanism or temperature distribution in the body.

In an embodiment, the data processing unit can be suitable to simulate an application of heat to at least a part of the body.

In another embodiment, the system can comprise a heat source such as a source of an electromagnetic field or any other heat transport carrier, for example focal ultrasound, laser beam, catheter, x-ray, infrared, microwaves, gamma radiation, or any other radiation with a wave length suitable to apply thermal energy to tissue, nano particles, colloids, or liposome.

In an embodiment, the imaging equipment can be suitable to obtaining images or imaging sequences with magnetic resonance Ti-weighted gradient-echo sequences or with magnetic resonance proton-frequency-shift alterations or with magnetic resonance tomography or with x-ray tomography.

The data processing unit can be suitable to determine and/or predict the temperature or heat distribution in at least a part of the body using the model of the body.

In an embodiment, the model of the body can be a perfusion model of the body obtained with magnetic resonance imaging or computer tomography, or a model based on diffusion coefficients or proton-frequency-shift alterations, both being obtained with magnetic resonance imaging.

In another embodiment, the data base is suitable to store tissue parameters of the body and/or a reference perfusion model of a reference body and/or a reference temperature model of a reference body.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference will now be made in detail to the exemplary embodiments of the invention illustrated in the accompanying drawings.

Figure 1:
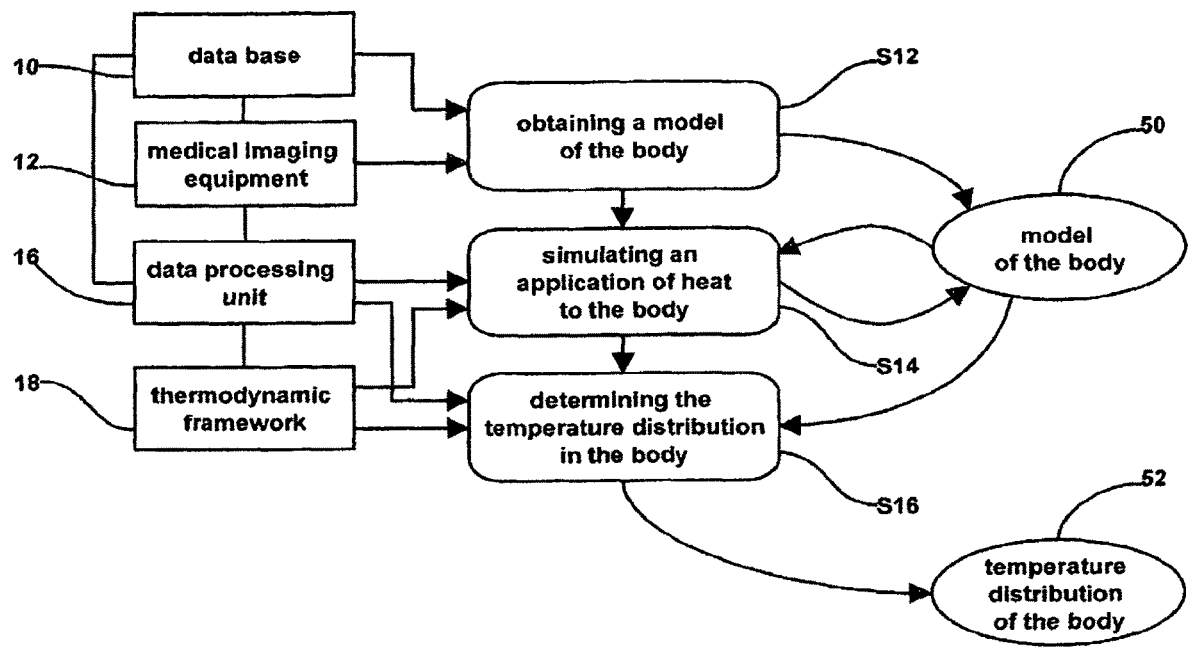
FIG. 1 illustrates a process of predicting or planning a temperature distribution in a body according to a first embodiment of the present invention.

In the embodiment illustrated in FIG. 1, the invention relates to a process of predicting or planning a temperature distribution 52 in a biologic tissue such as a body. The process comprises the steps of obtaining a model of the body 50 (S12), simulating an application of heat (S18) to the body (S16) and determining the temperature distribution 52 in the body (S16).

The model of the body 50 obtained in the initial step is related to or directed to a temperature distribution 52 in the body. The model comprises a 2D and/or 3D signal distribution in the body related to perfusion of the body. The model is obtained either from DTE-MRI images delivered by an imaging equipment 12, or from a data base 10.

Simulating an application of heat (S14) refers to simulating at the boundary of a simulation space including at least a part of the body such as the head, knee or another organ of a patient, a boundary condition for the heat distribution at the boundary of the simulation space. Simulating the application of heat additionally refers to simulating the heat propagation inside the simulation space. The targeted tissue usually is a tumour.

Determining the temperature distribution 52 in the body (S16) refers to determining and predicting the temperature or heat distribution in the body using the model of the body 50 by taking into account the simulated heat source. Simulating the application of heat (S14) requires a thermodynamic framework 18 such as a computer aided design system for thermodynamic simulations to simulate the heat propagation and/or distribution in the body.

In this embodiment, the heat is not physically applied to the body. Instead, as already mentioned, the application of heat is simulated.

Figure 2:
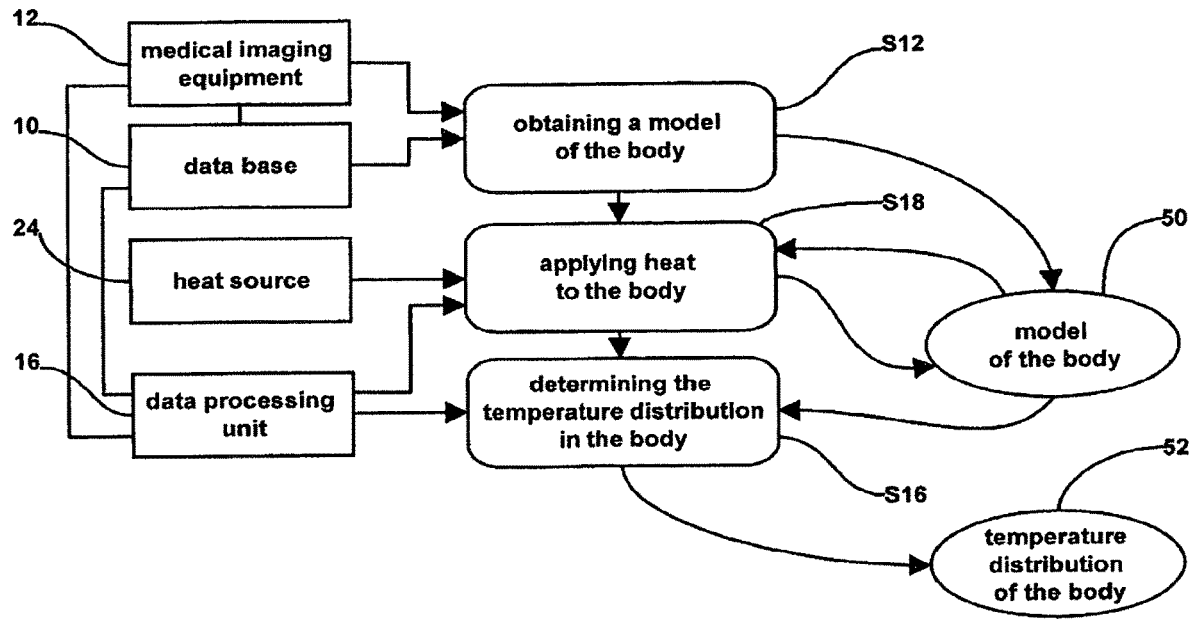
FIG. 2 illustrates a process of controlling or monitoring a temperature distribution in a body according to a second embodiment of the present invention.

In the embodiment illustrated in FIG. 2, the invention relates to a process of controlling or monitoring a temperature distribution 52 in a body. The body usually is part of the body such as an organ, for example liver, knee or brain of a patient.

Controlling the temperature distribution 52 in the body refers to setting up the parameters of the heat source 24 applying heat to the body so that a defined or desired spatial distribution or temporal progression of heat in the body is obtained. With tumour ablation or hyperthermia of a tumour the desired temperature distribution 52 is as far as possible at least 80 degrees Celsius inside the tumour and less than 41 degrees outside the tumour.

The process comprises the steps of obtaining a model of the body 50 (S12), applying heat to the body (S18), and determining the temperature distribution 52 in the body (S16).

Applying heat to the body (S18) refers to bringing the heat source 24 to or in the vicinity of the body so that the heat may reach or penetrate the body. The heat source 24 is a microwave source. The heat source generates at the boundary of a simulation space including at least a part of the body such as the head, knee or another organ of a patient, a boundary condition for the heat distribution at the boundary of the simulation space. The propagation and distribution of heat is obtained in the embodiment similarly to the embodiment exemplified in FIG. 1.

The step of obtaining a model of the body 50 (S12) concerns a perfusion model. The perfusion model is obtained from DTE-MRI images delivered by the medical imaging equipment 12 or obtained from the database 10.

Determining the temperature distribution 52 in the body (S16) refers to determining and/or predicting the temperature or heat distribution in the body using the model of the body 50 by taking into account the heat distribution at the boundary of the simulation space generated by the heat source 24.

In the embodiment shown in FIG. 2, the heat is physically applied to the body. But above this physical application of heat, the process of calculating the heat propagation and distribution in the body based on the heat distribution at the boundary of the simulation space corresponds to the process shown in FIG. 1.

Figure 3:
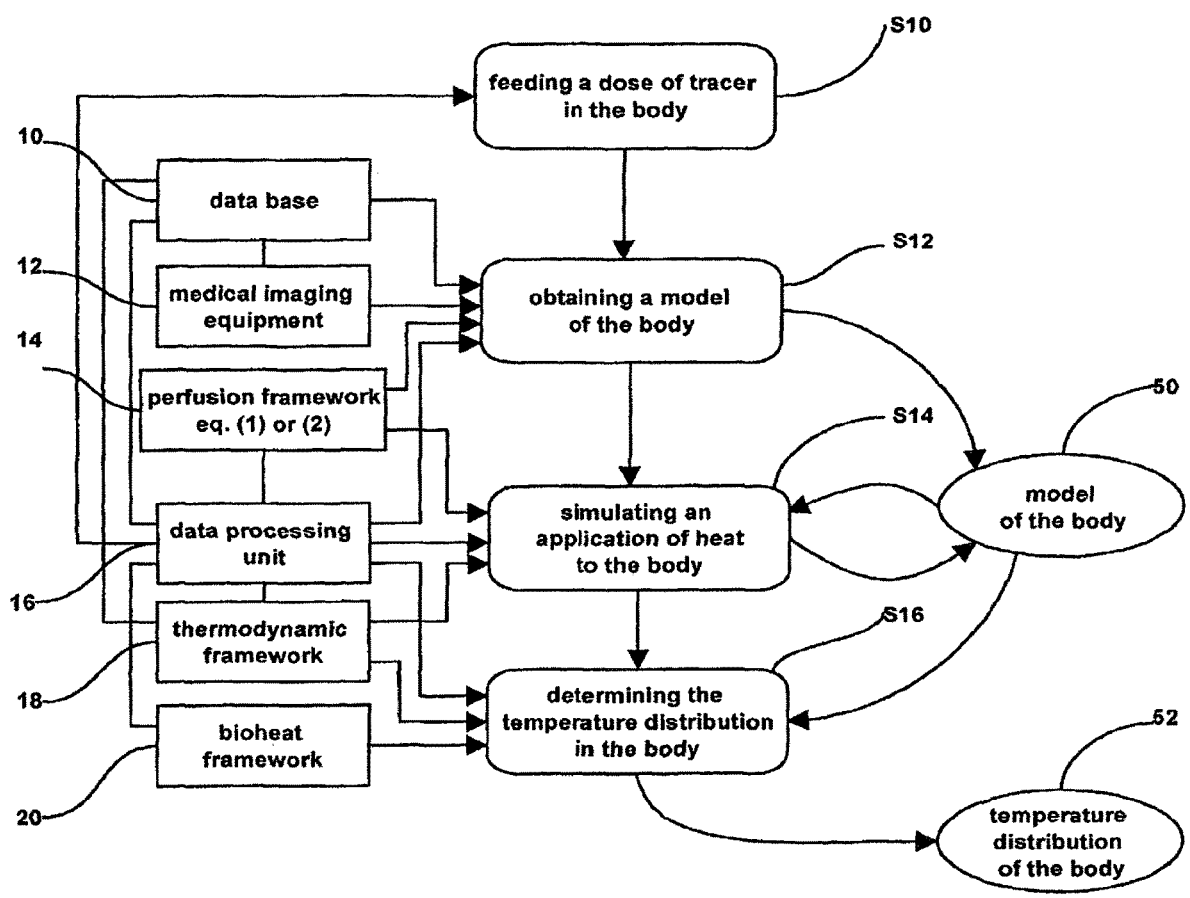
FIG. 3 illustrates the process of predicting or planning a temperature distribution in a body according to a third embodiment of the present invention.

In the embodiment illustrated in FIG. 3, the invention relates to a process of predicting or planning a temperature distribution 52 in a biologic tissue such as a body. This embodiment is similar to that shown in FIG. 1.

The initial step consists in feeding a contrast agent or tracer (S10) such as gadolinium (III) into the body. This step supports the procedure of obtaining DTE-MRI images from a patient, whereat the contrast agent is supposed to improve the imaging of blood perfusion in the body of the patient.

The step of obtaining the model of the body 50 (S12) comprises the application of a frame-work establishing a relation between the signal distributions in images obtained with a DIE-MRI imaging equipment 12 and the perfusion distribution in the body. Such a perfusion framework 14 is based on equations (1) or (2) or on similar equations establishing the relation between a signal distribution of a 2D or 3D image and a perfusion distribution.

The step of determining the temperature distribution 52 (S16) from the perfusion distribution of the body comprises the application of a framework establishing a relation between the perfusion distribution and the temperature distribution 52 in the body. Such a framework is based on a bioheat framework 20 such as equation (3). The dependency of the temperature from a signal distribution obtained from images or from the model of the body 50 is determined after obtaining a perfusion distribution as well as the tissue parameters of the body from the signal distribution shown in the DTE-MRI images.

Figure 4:
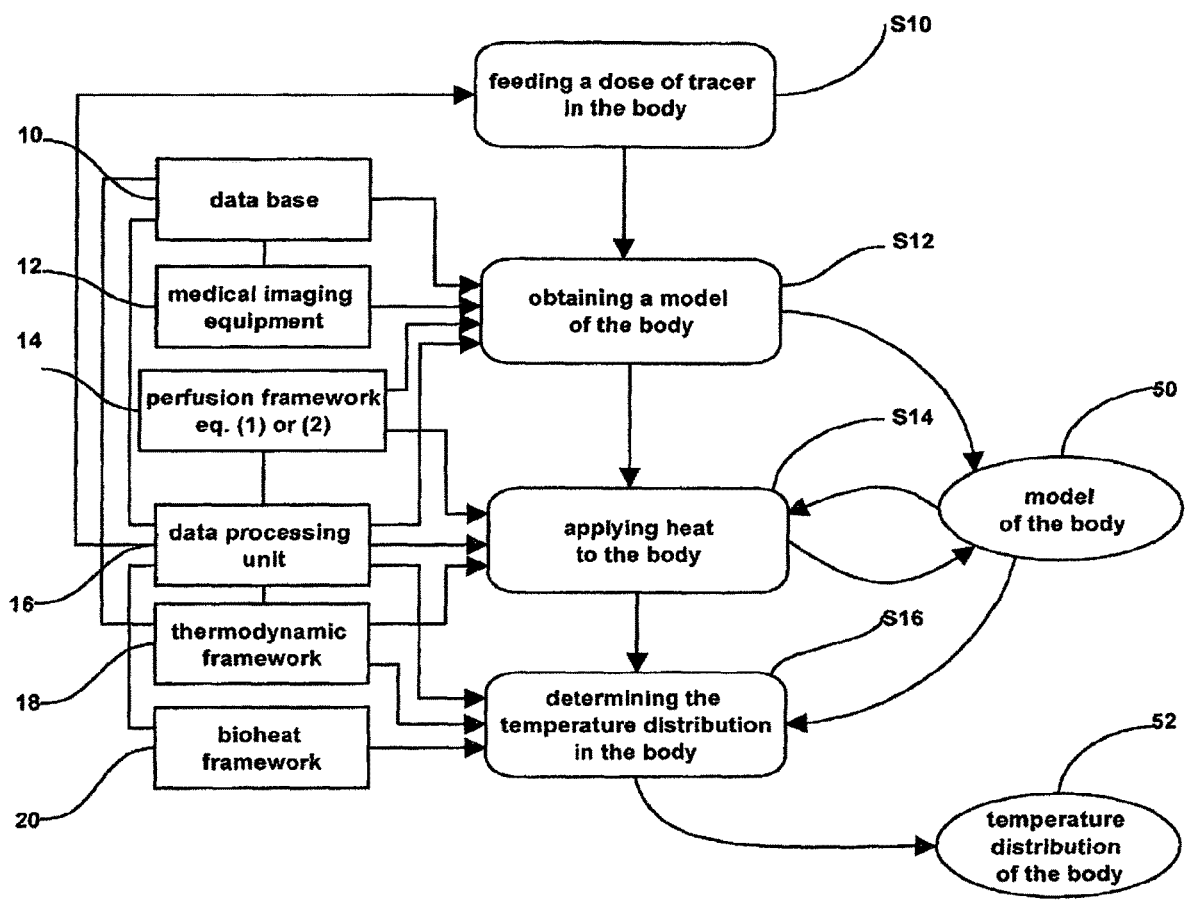
FIG. 4 illustrates the process of controlling or monitoring a temperature distribution in a body according to a fourth embodiment of the present invention.

In the embodiment illustrated in FIG. 4, the invention relates to a process of controlling or monitoring a temperature distribution 52 in a biologic tissue such as a body. This embodiment is based on that shown in FIG. 2 and is similar to that shown in FIG. 4. The embodiment shown in FIG. 4 differs from that shown in FIG. 3 in the way of treating the application of heat to the body: In one embodiment (FIG. 3), the application of heat is simulated, in the other (FIG. 4), the application of heat is physically performed.

Predicting and displaying temperature gradients in tissue together with information of the biological process triggered by any heat source 24 is implemented in a device and it is based on patient-specific information, heat source properties for example focal ultrasound, laser beam, catheter, x-ray, infrared, microwaves, gamma radiation, or any other radiation with a wave length suitable to apply thermal energy to tissue, nano particles, colloids, liposome. The application of heat (S18) is performed by electromagnetic fields and others heat transport carriers as well as any administrated agent supporting the heat transfer. In addition, the method also takes into account physiological tissue properties like heat capacity, vascular permeability, hydraulic conductivity, pore fraction and diffusivity. As embodiment the method predicts temperature and effects not only before and during treatment or heat transfer but also after its interruption.

An embodiment of the invention consists of the display of exposure time, necrotic tissue density, swelling degree, tumor size and others physiological or physical properties that can lead to modification or interruption of the treatment.

The invention is very useful to support treatment planning where thermal variations in tissue are expected (e.g. radiotherapy) to prevent and control side effects caused by an increase in temperature of tissue as well as to redefine and/or control automatically and in-situ the heat monitoring set-up. Such a monitoring of the temperature can facilitate many clinical procedures where a certain level of temperature has to be kept for a certain period of time, like ultrasound hyperthermia or local stimulation of the immune system and many more.

Any kind of heat source 24 like ultrasound, heat transport particles and other energy carriers can be used. The calculation of temperature is not solely based on perfusion but also on patient-specific information (age, sex) and properties like calorific capacity, diffusivity and other physiological and physical properties. Perfusion variations as well as other physiological properties are directly obtained by DCE-MRI and/or CT-Perfusion techniques during treatment.

Temperature profiles are obtained by the so-called perfusion techniques (DCE-MRI and/or CT-Perfusion). Also additional information can be in situ extracted regarding physiological properties of the tissue (e.g. necrosis, swelling), so it is possible to relate the temperature change with the underlying biological process. This allows tracking the effects that the heat transport entity has on tissue so one would be able to regulate and control in situ the heat source 24 according to this information.

Any administrated agent or combination supporting or affecting the heat transfer can be applied and agent specific information is processed to predict and display temperature gradients in tissue.

Physiological, metabolic, chemical and physical tissue properties like heat capacity, vascular permeability, hydraulic conductivity, pore fraction and diffusivity are processed to predict and display temperature gradients in tissue.

The information about the temperature gradients and its effects in tissue is used for treatment planning purposes, treatment controlling purposes, treatment follow up purposes, diagnostic purposes.

LIST OF REFERENCE SIGNS 10 data base
12 medical imaging equipment
14 perfusion framework
16 data processing unit
18 thermodynamic framework
20 bioheat framework
22 bolus
24 heat source
50 model of the body
52 temperature distribution of the body
S10 simulating a distribution of tracer in the body
S12 obtaining a model of the body
S14 simulating an application of heat to the body
S16 determining the temperature distribution in the body
S18 applying heat to the body

The invention claimed is:

1. A method performed by an apparatus comprising a computer system and a heat source operable to apply heat to an associated body part of an associated patient in accordance with a heat treatment plan, the computer system comprising a processing unit and a memory device operatively coupled with the processing unit, the memory device storing a database therein, the method comprising:

obtaining by the computer system imaging information of an image obtained of the associated body part of the associated patient;

identifying by the processing unit, from the imaging information of the associated body part of the associated patient, patient image data, the patient image data being representative of a set of patient tissue parameters of the associated body part of the associated patient and physical features of the associated body part of the associated patient comprising an extravascular-extracellular space (EES) of the associated body part of the associated patient;

retrieving by the computer system from the database a reference model of a temperature transport mechanism or a temperature distribution mechanism in a reference body part of a model patient, the reference model comprising data representative of tissue parameters of the model generic patient other than the associated patient and physical features of the model generic patient other than the associated patient;

generating by the processing unit, from the reference model and the imaging information of the associated body part of the associated patient, an individualized patient model by three-dimensional (3-D) rigid or non-rigid registration of: i) the reference model comprising the data representative of the tissue parameters and the physical features of the model generic patient other than the associated patient of the reference model with ii) the patient image data representative of the patient tissue parameters and the physical features of the associated body part of the associated patient, the individualized patient model modeling one or more of a temperature transport mechanism in the associated body part of the associated patient and/or a temperature distribution mechanism in the associated body part of the associated patient;

determining, by the processing unit based on simulating using a bioheat equation applying heat applied to specific spatial destinations in the individualized patient model as a simulated heat treatment, a simulated spatial heat distribution of the simulated heat in the treatment target tissue and in the non-treatment target tissue of the associated body part of the associated patient;

storing by the computer system the simulated heat treatment in the database as the heat treatment plan for use by the heat source to apply the heat to the associated body part of the associated patient based on the processing unit confirming that the simulated spatial heat distribution of the applied simulated heat in treatment and non-treatment target tissues matches a desired spatial distribution of heat in treatment and non-treatment target tissues of the associated body part of the associated patient; and operating the heat source based on the heat treatment plan stored in the database to apply heat to the associated body part of the associated patient to control a temperature distribution in the associated body part to obtain the desired spatial distribution of the heat in the treatment and non-treatment target tissues of the associated body part.

2. The method according to claim 1, wherein:

the obtaining the imaging information comprises:
  obtaining imaging information comprising a series of images of the associated body part of the associated patient comprising a first image of the associated body part obtained by an associated imaging device at a first time, a second image of the associated body part obtained by the associated imaging device at a second time after the first time, and a third image of the associated body part obtained by the associated imaging device at a third time after the second time;

the identifying the patient imaging data comprises:
  determining from the series of images changes in locations of a contrast agent administered at the second time to the associated body part as an exchange of the contrast agent between vascular spaces of the associated body part; and
  determining an extravascular-extracellular space (EES) of the associated body part as the determined exchange of the contrast agent between the vascular spaces of the associated body part.

3. The method according to claim 1, wherein the storing the simulated heat treatment in the database as the heat treatment plan comprises:
  storing the simulated heat treatment in the database as the heat treatment plan in accordance with the processing unit determining that:
    the simulated spatial heat distribution of the applied simulated heat in the treatment target tissue correlates with a temperature equal to or greater than a first critical temperature; and
    the simulated spatial heat distribution of the applied simulated heat in the non-treatment target tissue correlates with a temperature below a second critical temperature different than the first critical temperature.

4. The method according to claim 3, wherein the first critical temperature is about 80 degrees Celsius and the second critical temperature is about 41 degrees Celsius.

5. The method according to claim 1, wherein:
  the reference model of the temperature transport mechanism is a perfusion distribution model of the associated body part obtained with nuclear magnetic resonance or computer tomography; and
  the reference model of the temperature transport mechanism is a model based on diffusion coefficients or proton frequency-shift alterations, both being obtained with nuclear magnetic resonance.

6. The method according to claim 5, further comprising:
  determining a volume of necrosis in the treatment and non-treatment target tissues of the associated body part of the associated patient based on a time and temperature relationship therein; and
  adjusting the perfusion distribution model of the associated body part based on the determined volume of necrosis.

7. The method according to claim 1, wherein identifying the patient image data comprises:
  identifying by the processing unit, from the imaging information of the associated body part of the associated patient, patient image data being representative of a permeability surface area product of the endothelium of the associated body part of the associated patient.

8. A non-transitory computer-readable storage medium storing a set of instructions for developing a heat treatment plan for use by a system comprising a computer system and a heat source operable to apply heat to an associated body part of an associated patient in accordance with a heat treatment plan, the set of instructions when executed by one or more processors of the computer system, cause the one or more processors to perform a method comprising:
  obtaining by the computer system imaging information of an image obtained of the associated body part of the associated patient;
  identifying by the processing unit, from the imaging information of the associated body part of the associated patient, patient image data, the patient image data being representative of a set of patient tissue parameters of the associated body part of the associated patient and physical features of the associated body part of the associated patient comprising an extravascular-extracellular space (EES) of the associated body part of the associated patient;
  retrieving by the computer system from the database a reference model of a temperature transport mechanism or a temperature distribution mechanism in a reference body part of a model patient, the reference model comprising data representative of tissue parameters of the model generic patient other than the associated patient and physical features of the model generic patient other than the associated patient;

generating by the processing unit, from the reference model and the imaging information of the associated body part of the associated patient, an individualized patient model by three-dimensional (3-D) rigid or non-rigid registration of: i) the reference model comprising the data representative of the tissue parameters and the physical features of the model generic patient other than the associated patient of the reference model with ii) the patient image data representative of the patient tissue parameters and the physical features of the associated body part of the associated patient, the individualized patient model modeling one or more of a temperature transport mechanism in the associated body part of the associated patient and/or a temperature distribution mechanism in the associated body part of the associated patient;

determining, by the processing unit based on simulating using a bioheat equation applying heat applied to specific spatial destinations in the individualized patient model as a simulated heat treatment, a simulated spatial heat distribution of the simulated heat in the treatment target tissue and in the non-treatment target tissue of the associated body part of the associated patient; and storing by the computer system the simulated heat treatment in the database as the heat treatment plan for use by the heat source to apply the heat to the associated body part of the associated patient based on the processing unit confirming that the simulated spatial heat distribution of the applied simulated heat in treatment and non-treatment target tissues matches a desired spatial distribution of heat in treatment and non-treatment target tissues of the associated body part of the associated patient; and operating the heat source based on the heat treatment plan stored in the database to apply heat to the associated body part of the associated patient to control a temperature distribution in the associated body part to obtain the desired spatial distribution of the heat in the treatment and non-treatment target tissues of the associated body part.

9. The non-transitory computer-readable storage medium according to claim 8, wherein:
the obtaining the imaging information comprises:
obtaining imaging information comprising a series of images of the associated body part of the associated patient comprising a first image of the associated body part obtained by an associated imaging device at a first time, a second image of the associated body part obtained by the associated imaging device at a second time after the first time, and a third image of the associated body part obtained by the associated imaging device at a third time after the second time;
the identifying the patient imaging data comprises:
determining from the series of images changes in locations of a contrast agent administered at the second time to the associated body part as an exchange of the contrast agent between vascular spaces of the associated body part; and
determining an extravascular-extracellular space (EES) of the associated body part as the determined exchange of the contrast agent between the vascular spaces of the associated body part.

10. The non-transitory computer-readable storage medium according to claim 8, wherein the storing the simulated heat treatment in the database as the heat treatment plan comprises:
storing the simulated heat treatment in the database as the heat treatment plan in accordance with the processing unit determining that:
the simulated spatial heat distribution of the applied simulated heat in the treatment target tissue correlates with a temperature equal to or greater than a first critical temperature; and
the simulated spatial heat distribution of the applied simulated heat in the non-treatment target tissue correlates with a temperature below a second critical temperature different than the first critical temperature.

11. The non-transitory computer-readable storage medium according to claim 10, wherein the first critical temperature is about 80 degrees Celsius and the second critical temperature is about 41 degrees Celsius.

12. The non-transitory computer-readable storage medium according to claim 8, wherein:
the reference model of the temperature transport mechanism is a perfusion distribution model of the associated body part obtained with nuclear magnetic resonance or computer tomography; and
the reference model of the temperature transport mechanism is a model based on diffusion coefficients or proton frequency-shift alterations, both being obtained with nuclear magnetic resonance.

13. The non-transitory computer-readable storage medium according to claim 12, further comprising:
determining a volume of necrosis in the treatment and non-treatment target tissues of the associated body part of the associated patient based on a time and temperature relationship therein; and
adjusting the perfusion distribution model of the associated body part based on the determined volume of necrosis.

14. The non-transitory computer-readable storage medium according to claim 8, wherein identifying the patient image data comprises:
identifying by the processing unit, from the imaging information of the associated body part of the associated patient, patient image data being representative of a permeability surface area product of the endothelium of the associated body part of the associated patient.

15. An apparatus comprising:
a heat source operable to apply heat to an associated body part of an associated patient in accordance with a heat treatment plan; and
a computer system operably coupled with the heat source, the computer system comprising one or more processing units and a memory device operatively coupled with the one or more processing units, the memory device storing a set of instructions and a database therein, wherein the set of instructions when executed by the one or more processors of the computer system, cause the one or more processors to:
obtain by the computer system imaging information of an image obtained of the associated body part of the associated patient;
identify, from the imaging information of the associated body part of the associated patient, patient image data, the patient image data being representative of a set of patient tissue parameters of the associated body part of the associated patient and physical features of the associated body part of the associated patient comprising an extravascular-extracellular space (EES) of the associated body part of the associated patient;

retrieve from the database a reference model of a temperature transport mechanism or a temperature distribution mechanism in a reference body part of a model patient, the reference model comprising data representative of tissue parameters of the model generic patient other than the associated patient and physical features of the model generic patient other than the associated patient;

generate, from the reference model and the imaging information of the associated body part of the associated patient, an individualized patient model by three-dimensional (3-D) rigid or non-rigid registration of: i) the reference model comprising the data representative of the tissue parameters and the physical features of the model generic patient other than the associated patient of the reference model with ii) the patient image data representative of the patient tissue parameters and the physical features of the associated body part of the associated patient, the individualized patient model modeling one or more of a temperature transport mechanism in the associated body part of the associated patient and/or a temperature distribution mechanism in the associated body part of the associated patient;

determine, by the processing unit based on simulating using a bioheat equation applying heat applied to specific spatial destinations in the individualized patient model as a simulated heat treatment, a simulated spatial heat distribution of the simulated heat in the treatment target tissue and in the non-treatment target tissue of the associated body part of the associated patient; and store the simulated heat treatment in the database as the heat treatment plan for use by the heat source to apply the heat to the associated body part of the associated patient based on the processing unit confirming that the simulated spatial heat distribution of the applied simulated heat in the treatment and non-treatment target tissues matches a desired spatial distribution of heat in the treatment and non-treatment target tissues of the associated body part of the associated patient; and operate the heat source based on the heat treatment plan stored in the database to apply heat to the associated body part of the associated patient to control a temperature distribution in the associated body part to obtain the desired spatial distribution of the heat in the treatment and non-treatment target tissues of the associated body part.

16. The apparatus according to claim 15, wherein the set of instructions when executed by the one or more processors of the computer system, cause the one or more processors to obtain the imaging information by:

obtaining imaging information comprising a series of images of the associated body part of the associated patient comprising a first image of the associated body part obtained by an associated imaging device at a first time, a second image of the associated body part obtained by the associated imaging device at a second time after the first time, and a third image of the associated body part obtained by the associated imaging device at a third time after the second time;

identify the patient imaging data by:

determining from the series of images changes in locations of a contrast agent administered at the second time to the associated body part as an exchange of the contrast agent between vascular spaces of the associated body part; and determining an extravascular-extracellular space (EES) of the associated body part as the determined exchange of the contrast agent between the vascular spaces of the associated body part.

17. The apparatus according to claim 15, wherein the set of instructions when executed by the one or more processors of the computer system, cause the one or more processors to store the simulated heat treatment in the database as the heat treatment plan by:

storing the simulated heat treatment in the database as the heat treatment plan in accordance with the one or more processing units determining that:

the simulated spatial heat distribution of the applied simulated heat in the treatment target tissue correlates with a temperature equal to or greater than a first critical temperature; and the simulated spatial heat distribution of the applied simulated heat in the non-treatment target tissue correlates with a temperature below a second critical temperature different than the first critical temperature.

18. The apparatus according to claim 15, wherein the set of instructions when executed by the one or more processors of the computer system, cause the one or more processors to store the simulated heat treatment in the database as the heat treatment plan by:

storing the simulated heat treatment in the database as the heat treatment plan in accordance with the one or more processing units determining that:

the simulated spatial heat distribution of the applied simulated heat in the treatment target tissue correlates with a temperature equal to or greater than about 80 degrees Celsius; and the simulated spatial heat distribution of the applied simulated heat in the non-treatment target tissue correlates with a temperature below a temperature of about 41 degrees Celsius.

19. The apparatus according to claim 15, wherein:

the reference model of the temperature transport mechanism is a perfusion distribution model of the associated body part obtained with nuclear magnetic resonance or computer tomography;

the reference model of the temperature transport mechanism is a model based on diffusion coefficients or proton frequency-shift alterations, both being obtained with nuclear magnetic resonance; and the set of instructions when executed by the one or more processors of the computer system, cause the one or more processors to:

determine a volume of necrosis in the treatment and non-treatment target tissues of the associated body part of the associated patient based on a time and temperature relationship therein; and adjust the perfusion distribution model of the associated body part based on the determined volume of necrosis.

20. The apparatus according to claim 15, wherein the set of instructions when executed by the one or more processors of the computer system, cause the one or more processors to identify the patient image data by:

identifying by the processing unit, from the imaging information of the associated body part of the associated patient, patient image data being representative of a permeability surface area product of the endothelium of the associated body part of the associated patient.

\* \* \* \* \*